United States Patent [19]

Imai et al.

[11] Patent Number: 4,506,032

[45] Date of Patent: Mar. 19, 1985

[54] DEHYDROGENATION CATALYST COMPOSITION

[75] Inventors: Tamotsu Imai, Mt. Prospect, Ill.; Chi-Wen Hung, San Rafael, Calif.

[73] Assignee: UOP Inc., Des Plaines, Ill.

[21] Appl. No.: 541,858

[22] Filed: Oct. 14, 1983

Related U.S. Application Data

[60] Division of Ser. No. 477,699, Mar. 22, 1983, Pat. No. 4,430,517, which is a continuation-in-part of Ser. No. 326,969, Dec. 2, 1981, abandoned.

[51] Int. Cl.$^3$ .................... B01J 27/04; B01J 27/08; B01J 27/10
[52] U.S. Cl. .................................. 502/223; 502/226; 502/227
[58] Field of Search ............... 502/226, 227, 230, 223

[56] References Cited

U.S. PATENT DOCUMENTS

| | | | |
|---|---|---|---|
| 3,892,657 | 7/1975 | Wilhelm | 502/230 X |
| 3,909,451 | 9/1975 | Wilhelm | 502/227 X |
| 3,998,900 | 12/1976 | Wilhelm | 502/227 X |
| 4,329,258 | 5/1982 | Engelhard et al. | 502/226 |

*Primary Examiner*—Patrick Garvin
*Attorney, Agent, or Firm*—James R. Hoatson, Jr.; William H. Page, II

[57] ABSTRACT

This invention relates to a new catalyst for converting hydrocarbons. The catalyst comprises a platinum group component, a Group IVA component, especially tin, an alkali or alkaline earth component, more than 0.2 weight %, calculated on an elemental basis, of a halogen component and a porous carrier material, wherein the atomic ratio of the alkali or alkaline earth component to the platinum group component is more than 10. The catalyst is particularly useful for dehydrogenating paraffins having from 2 to 5 or more carbon atoms to the corresponding mono-olefins, or for dehydrogenating mono-olefins having from 3 to 5 or more carbon atoms to the corresponding di-olefins.

14 Claims, 6 Drawing Figures

Time, Hours On Stream

Time, Hours On Stream

DEHYDROGENATION CATALYST COMPOSITION

CROSS-REFERENCE TO RELATED APPLICATION

This application is a Division of our prior copending application Ser. No. 477,699 filed Mar. 22, 1983 and now U.S. Pat. No. 4,430,517, which is a Continuation-In-Part of our prior application Ser. No. 326,969 filed Dec. 2, 1981, now abandoned, both prior references incorporated herein by reference.

BACKGROUND OF THE INVENTION

(1) Field of the Invention

This invention pertains to the conversion of hydrocarbons, especially the dehydrogenation of dehydrogenatable hydrocarbons, in the presence of a catalyst composite. This invention also pertains to a new catalyst composite and a method of making it.

Dehydrogenating hydrocarbons is an important commercial hydrocarbon conversion process because of the great demand for dehydrogenated hydrocarbons for the manufacture of various chemical products such as detergents, high octane gasolines, pharmaceutical products, plastics, synthetic rubbers, and other products well-known to those skilled in the art. One example of this process is dehydrogenating isobutane to produce isobutylene which can be polymerized to provide tackifying agents for adhesives, viscosity-index additives for motor oils and impact-resistant and anti-oxidant additives for plastics.

(2) Description of the Prior Art

It is well-known to catalyze the conversion of hydrocarbons with solid catalysts comprising platinum group metals. For example, U.S. Pat. Nos. 2,479,109 and 2,479,110 disclose a catalyst comprising platinum on alumina with combined halogen for catalyzing reforming, hydrogenating, hydrocracking, oxidizing and dehydrogenating reactions. The term "reforming" in these patents means simultaneously dehydrogenating, isomerizing, cyclizing and cracking a gasoline feedstock. The combined halogen component of this catalyst contributes to a controlled type of cracking activity. The halogen content is preferably maintained below about 8 weight % of the alumina to avoid excessive side reactions, including cracking reactions, which result in excessive gas formation and low liquid volume yield of reformed products. These patents do not disclose utilizing an alkali or alkaline earth component.

U.S. Pat. No. 2,602,772 discloses converting hydrocarbons, especially reforming and hydrocracking hydrocarbons, with a catalyst comprising platinum, not more than 1 weight % of an oxide of an alkaline earth metal or magnesium and from about 0.1 to about 8 weight % combined halogen on alumina. According to this patent catalysts containing an alkaline earth metal or magnesium oxide produced less carbon, or coke, after 3 days of reforming operations. The halogen content for catalysts of this patent is from 0.3 to 3 weight %, preferably between 0.6 and 2.3 weight %. This patent does not disclose utilizing a Group IVA component.

U.S. Pat. No. 2,930,763 discloses a two-step process for reforming hydrocarbons. In the first step a hydrocarbon fraction containing unsaturated compounds and/or nitrogen, sulfur or oxygen compounds is contacted with hydrogen in the presence of a catalyst comprising platinum and an alkali metal component on alumina to hydrogenate and saturate the unsaturated compounds and/or reduce the nitrogen, sulfur or oxygen content of the hydrocarbon fraction. In the second step of this process the treated hydrocarbon fraction from the first step is contacted at reforming conditions with a conventional reforming catalyst comprising platinum and combined halogen on alumina. Optionally the catalyst utilized in the first step may contain halogen. A catalyst consisting essentially of alumina, from about 0.01% to about 1% by weight of platinum, from about 0.1% to about 1% by weight of combined halogen, and from about 0.01% to about 1% by weight of an alkali metal is recited in claim 2 of this patent. This patent also does not disclose utilizing a Group IVA component.

U.S. Pat. No. 3,531,543 discloses dehydrogenating hydrocarbons with a catalyst comprising platinum, tin and neutralized metal oxide carrier. The preferred carriers are oxide materials whose intrinsic acidity is substantially neutralized by an alkali or alkaline earth metal component. Pure alumina, for example, has such intrinsic acidity. (cf. Pines and Haag, *Journal of the American Chemical Society*, 82, 2471 (1960)). For example, alumina catalyzed the skeletal isomerization of olefins, dehydrates alcohols and strongly chemisorbs amines. Also, with increasing amounts of alkali present there is a parallel decrease in these acidic alumina properties. Preferably the carrier of this patent is a non-acidic lithiated alumina. Preferably, the catalysts of this patent are prepared from halogen-free compounds. Compounds containing halogen may be used to manufacture the catalyst provided the halogen residue is efficiently removed from the final catalyst composite.

U.S. Pat. No. 3,745,112 discloses a catalyst for reforming hydrocarbons which comprises a platinum group component, a tin component and a halogen component with a porous carrier material. This patent discloses also that a platinum-tin-alkali or alkaline earth composite is a particularly effective catalyst for dehydrogenating hydrocarbons. In the dehydrogenation catalyst composite of this patent wherein the alkali or alkaline earth component is added the amount of halogen, if not entirely eliminated, is minimized in order to minimize or neutralize the acidic functions of the alumina and halogen components which tend to promote hydrocarbon cracking and isomerization side reactions which are not desired in commercial dehydrogenation processes.

U.S. Pat. No. 3,892,657 discloses that indium is a good promoter for platinum group-containing catalysts when the atomic ratio of indium to platinum is from about 0.1:1 to about 1:1. This patent discloses also that a Group IVA component selected from the group of germanium, tin, and lead can be added to the acidic form of the indium-containing catalysts for reforming applications. The acidic form of this catalyst, then, comprises a platinum group component, a Group IVA component, an indium component, a halogen component and a porous carrier material. The acidic catalyst contains up to about 3.5 weight % halogen for reforming applications and up to about 10 weight % halogen for isomerization and cracking applications. In the dehydrogenation catalyst of this patent wherein the alkali or alkaline earth component is added, however, the halogen content is maintained at the lowest possible value (about 0.1 weight %).

U.S. Pat. No. 3,909,451 discloses a new method for making a dehydrogenation catalyst comprising a platinum component, a tin component and an alkali or alkaline earth component. In Example V this patent discloses a platinum, tin and potassium composition comprising less than 0.2 weight % combined chloride.

U.S. Pat. Nos. 4,329,258 and 4,363,721 disclose a catalyst comprising a platinum group metal, tin, an alkali or alkaline earth metal and combined halogen element with a refractory oxidemineral carrier. The atomic ratio of alkali or alkaline earth metal to platinum group metal for catalysts of these patents is from 0.2 to 10. The patentees discovered that parts-per-million quantities of alkali or alkaline earth component added to catalyst containing a platinum group metal, tin and halogen helped increase the $C_5+$ yield in a reforming process.

British Pat. No. 1 499 297 discloses a dehydrogenation catalyst comprising platinum, at least one of the elements gallium, indium and thallium, and an alkali metal, especially lithium or potassium, with alumina as the carrier material. The catalysts of this patent also contain a halogen in an amount of from 0.01 to 0.1 weight %. The halogen content is purposely reduced to within this low weight % range in order to increase the selectivity and stability of the catalyst.

In the prior art dehydrogenation catalysts acknowledged above comprising a platinum group component, a Group IVA component and an alkali or alkaline earth component wherein the atomic ratio of the alkali or alkaline earth component to the platinum group component is more than 10, then, the halogen component has been eliminated completely or otherwise maintained at the lowest possible level, generally less than 0.1 weight %, and always less than 0.2 weight %, calculated on an elemental basis.

Surprisingly, we discovered that incorporating more halogen component than was previously present in these types of dehydrogenation catalysts provided catalysts with improved activity and selectivity characteristics.

SUMMARY OF THE INVENTION

This invention relates to a new catalyst for converting hydrocarbons, especially for dehydrogenating hydrocarbon. The catalyst comprises a platinum group component, a Group IVA component, an alkali or alkaline earth component, more than 0.2 weight %, calculated on an elemental basis, of a halogen component and a porous carrier material, wherein the atomic ratio of the alkali or alkaline earth component to the platinum group component is more than 10. The catalyst is particularly useful for dehydrogenating paraffins having from 2 to 5 or more carbon atoms to the corresponding mono-olefins or for dehydrogenating mono-olefins having from 3 to 5 or more carbon atoms to the corresponding di-olefins.

DETAILED DESCRIPTION OF THE INVENTION

Figure 1:
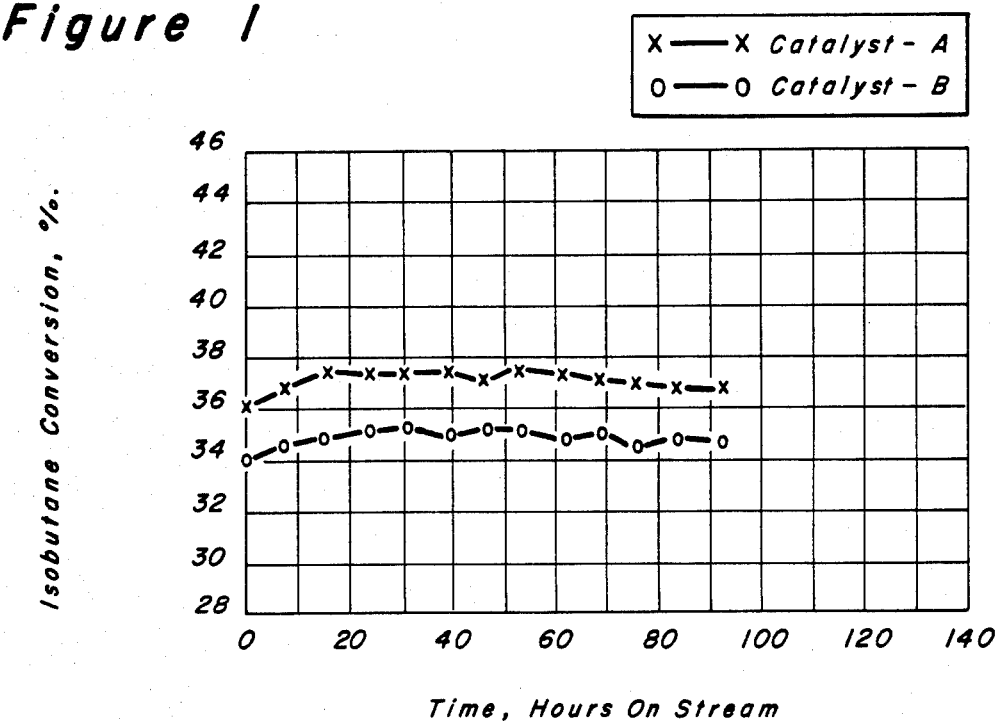
FIGS. 1-6 illustrate results from tests with catalysts of this invention, namely catalysts "A", "C" and "E" compared with results from tests with prior art catalysts "B", "D" and "F", respectively.

Heterogeneous catalysis practice, that is, catalyzing reactions of liquid or gaseous reactants with solid catalysts, is important to industry. For many years persons skilled in the art of hydrocarbon conversion, for example, have endeavored to discover and develop new hydrocarbon conversion catalysts with improved performance characteristics. Many of these persons are highly trained in one or more of a wide variety of disciplines including, for example, organic and inorganic chemistry, solid state and surface physics, ceramics, metallurgy and chemical engineering. Notwithstanding this high level of skill in the art, hydrocarbon conversion catalysis, like other fields of heterogeneous catalysis, continues to be "a vast and confusing field replete with an enormous quantity of perhaps significant but empirical facts intermixed with perhaps useful theories." (C.N. Satterfield, Heterogeneous Catalysis in Practice, preface (1980)).

Consequently, significant contributions to the art of heterogeneous hydrocarbon conversion catalysis have generally resulted from empirical discoveries and developments rather than from theoretical extrapolations.

Our contribution to this field of art is that we have discovered a new catalyst for dehydrogenating hydrocarbons. The catalyst comprises a platinum group component, a Group IVA component, an alkali or alkaline earth component, more than 0.2 weight %, calculated on an elemental basis, of a halogen component and a porous carrier material, wherein the atomic ratio of the alkali or alkaline earth component to the platinum group component is more than 10. The platinum group component is preferably present in the final composite in an amount, calculated on an elemental basis, of about 0.01 to 5 weight %; the Group IVA component is preferably present in an amount of about 0.01 to 5 weight %; the alkali or alkaline earth component is preferably present in an amount of about 0.01 to 15 weight %; and the halogen component is present preferably in an amount of about 0.2 to 15 weight %. Dehydrogenation conditions include a temperature of from about 400° to 900° C., a pressure of from about 0.01 to 10 atmospheres and a liquid hourly space velocity (LHSV - calculated on the basis of the volume amount, as a liquid at standard conditions, of hydrocarbon charged to the dehydrogenation zone per hour divided by the volume of the catalyst bed utilized in the dehydrogenation zone) of from about 0.1 to 100 hr.$^{-1}$. The hydrocarbons to be dehydrogenated are dehydrogenatable hydrocarbons having from 2 to 30 or more carbon atoms including paraffins, alkylaromatics, naphthenes and olefins. One group of hydrocarbons which can be dehydrogenated with the catalyst is the group of normal paraffins having from 2 to 30 or more carbon atoms. The catalyst is particularly useful for dehydrogenating paraffins having from 2 to 5 or more carbon atoms to the corresponding mono-olefins or for dehydrogenating mono-olefins having from 3 to 5 or more carbon atoms to the corresponding di-olefins.

Our invention, then, is a new catalyst composition which comprises a platinum group component, a Group IVA component, an alkali or alkaline earth component, more than 0.2 weight %, calculated on an elemental basis, of a halogen component and a porous carrier material, wherein the atomic ratio of the alkali or alkaline earth component to the platinum group component is more than 10.

To be commercially successful a dehydrogenation catalyst must satisfy three requirements, namely high activity, high selectivity and good stability. Activity is a measure of the catalyst's ability to help convert reactants into products at a specified severity level where severity level means the reaction conditions used—that is, the temperature, pressure, contact time and presence of diluents such as hydrogen if any. For dehydrogenation catalyst activity we measured the conversion, or disappearance, of paraffins in percent relative to the amount of paraffins in the feedstock. Selectivity is a measure of the catalyst's ability to help convert reactants into desired product or products relative to the amount of reactants charged or converted. For catalyst selectivity we measured the amount of olefins in the product, in mol percent, relative to the total mols of the paraffins converted. Stability is a measure of the rate of change with time on stream of the activity and selectivity parameters—the smaller rates implying the more stable catalysts.

Since dehydrogenation of hydrocarbons is an endothermic reaction and conversion levels are limited by chemical equilibrium, it is desirable in order to achieve high conversion to operate at high temperatures and low hydrogen partial pressures. At such severe conditions it is difficult to maintain high activity and selectivity for long periods of time because undesirable side reactions such as aromatization, cracking, isomerization and coke formation increase. Therefore, there is a considerable demand for a new hydrocarbon dehydrogenation catalyst with improved activity, selectivity and stability characteristics. The catalyst of our invention, that is, a dehydrogenation catalyst comprising a platinum group component, a Group IVA component, an alkali or alkaline earth component, more than 0.2 weight %, calculated on an elemental basis, of a halogen component and a porous carrier material wherein the atomic ratio of the alkali or alkaline earth component to the platinum group component is more than 10, will answer to such a demand.

Regarding the platinum group component of our catalyst composite, it may be selected from the group of platinum or palladium or iridium or rhodium or osmium or ruthenium or mixtures thereof. Platinum, however, is the preferred platinum group component. We believe that substantially all of the platinum group component exists within the catalyst in the elemental metallic state.

Preferably the platinum group component is well dispersed throughout the catalyst. The platinum group component generally will comprise about 0.01 to 5 weight %, calculated on an elemental basis, of the final catalytic composite. Preferably the catalyst comprises about 0.1 to 1 weight % platinum.

The platinum group component may be incorporated in the catalytic composite in any suitable manner such as, for example, by coprecipitation or cogelation, ion exchange or impregnation, or deposition from a vapor phase or from an atomic source or by like procedures either before, while or after other catalytic components are incorporated. The preferred method of incorporating the platinum group component is to impregnate the carrier material with a solution or suspension of a decomposable compound of a platinum group metal. For example, platinum may be added to the support by commingling the latter with an aqueous solution of chloroplatinic acid. Another acid, for example, nitric acid or other optional components may be added to the impregnating solution to further assist in dispersing or fixing the platinum group component in the final catalyst composite.

Regarding the Group IVA component, it may be selected from the group of germanium or tin or lead or mixtures thereof. Tin, however, is the preferred Group IVA component. We believe the Group IVA component exists within the catalyst in an oxidation state above that of the elemental metal. The Group IVA component may be present as a compound such as the oxide, for example, or combined with the carrier material or with the other catalytic components. Preferably the Group IVA component is well dispersed throughout the catalyst. The Group IVA component generally will comprise about 0.01 to 5 weight %, calculated on an elemental basis, of the final catalyst composite. Preferably the catalyst comprises about 0.2 to 2 weight % tin.

The Group IVA component may be incorporated in the catalytic composite in any suitable manner such as, for example, by coprecipitation or cogelation, ion exchange or impregnation or by like procedures either before, while or after other catalytic components are incorporated. A preferred method of incorporating the tin component is cogelling it during preparation of the porous carrier material. For example, tin may be incorporated in an alumina carrier material by mixing a soluble tin compound such as stannous or stannic chloride with an alumina hydrosol, adding a gelling agent such as hexamethylenetetramine and dropping the mixture into an oil bath to form spheres containing alumina and tin. A preferred method of incorporating the germanium component is to impregnate the carrier material with a solution or suspension of a decomposable compound of germanium such as germanium tetrachloride dissolved in an alcohol. Likewise, the lead component may be impregnated from a solution of lead nitrate in water.

Regarding the alkali or alkaline earth component, it may be selected from the group of cesium, rubidium, potassium, sodium and lithium or from the group of barium, strontium, calcium and magnesium or mixtures of components from either or both of these groups. Lithium, sodium, potassium, cesium and magnesium, however, are the preferred alkali or alkaline earth components. We believe that the alkali or alkaline earth component exists in the final catalytic composite in an oxidation state above that of the elemental metal. The alkali or alkaline earth component may be present as a compound such as the oxide, for example, or combined with the carrier material or with the other catalytic components.

Preferably the alkali or alkaline earth component is well dispersed throughout the catalytic composite. The alkali or alkaline earth component generally will comprise about 0.01 to 15 weight %, calculated on an elemental basis, of the final catalytic composite. Preferably the catalyst comprises about 1 to 3 weight % potassium.

The alkali or alkaline earth component may be incorporated in the catalytic composite in any suitable manner such as, for example, by coprecipitation or cogelation, by ion exchange or impregnation, or by like procedures either before, while or after other catalytic components are incorporated. A preferred method of incorporating the potassium component is to impregnate the carrier material with a solution of potassium nitrate.

In contradistinction to reforming or isomerization catalysts of the prior art, the catalyst of our invention comprises an atomic ratio of alkali or alkaline earth component to platinum group component of more than 10. In the prior art catalysts comprising a platinum group component and an alkali or alkaline earth component, on the other hand, the amount of the alkali or alkaline earth component was purposely maintained below this level. This is because addition of the alkali or alkaline earth component tends to decrease the acidity of these catalysts, which acidity is responsible for accelerating isomerization and cracking reactions. For reforming and isomerization catalysts it is desired to maintain some substantial amount of catalyst acidity, so the atomic ratio of alkali or alkaline earth component to platinum group component for these catalysts has been maintained at less than or equal to 10. For our catalyst, however, the atomic ratio of the alkali or alkaline earth component to the platinum group component is preferably from about 15 to about 25.

Regarding the porous carrier material, it is preferably a porous, absorptive support with high surface area of from about 25 to about 500 m²/g. The porous carrier material should be relatively refractory to the conditions utilized in the hydrocarbon conversion process. It is intended to include within the scope of our invention the use of carrier materials which have traditionally been utilized in hydrocarbon conversion catalysts such as, for example; (1) activated carbon, coke, or charcoal; (2) silica or silica gel, silicon carbide, clays, and silicates, including synthetically prepared and naturally occurring ones, which may or may not be acid treated, for example, attapulgus clay, china clay, diatomaceous earth, fuller's earth, kaolin, kieselguhr, etc.; (3) ceramics, procelain, crushed firebrick, bauxite; (4) refractory inorganic oxides such as alumina, titanium dioxide, zirconium dioxide, chromium oxide, beryllium oxide, vanadium oxide, cerium oxide, hafnium oxide, zinc oxide, magnesia, boria, thoria, silica-alumina, silica-magnesia, chromiaalumina, alumina-boria, silica-zirconia, etc.; (5) crystalline zeolitic aluminosilicates such as naturally occurring or synthetically prepared mordenite and/or faujasite, for example, either in the hydrogen form or in a form which has been exchanged with metal cations; (6) spinels such as $MgAl_2O_4$, $FeAl_2O_4$, $ZnAl_2O_4$, $CaAl_2O_4$, and other like compounds having the formula $MO-Al_2O_3$ where M is a metal having a valence of 2; and (7) combinations of materials from one or more of these groups. The preferred carrier material for our catalyst is alumina, especially gamma- or eta-alumina.

The preferred alumina carrier material may be prepared in any suitable manner from synthetic or naturally occurring raw materials. The carrier may be formed in any desired shape such as spheres, pills, cakes, extrudates, powders, granules, etc., and it may be utilized in any particle size. A preferred shape of alumina is the sphere. A preferred particle size is about 1/16 inch in diameter, though particles as small as about 1/32 inch, and smaller, may also be utilized.

To make alumina spheres aluminum metal is converted into an alumina sol by reacting it with a suitable peptizing acid and water, and then dropping a mixture of the resulting sol and a gelling agent into an oil bath to form spherical particles of an alumina gel which are easily converted into the preferred gamma- or eta-alumina carrier material by known methods including aging, drying and calcining. To make alumina cylinders, an alumina powder is mixed with water and enough of a suitable peptizing agent such as nitric acid, for example, until an extrudable dough is formed. The dough is then extruded through a suitably-sized die and cut to form extrudate particles. Other shapes of the alumina carrier material may also be prepared by conventional methods. After the alumina particles are shaped generally they are dried and calcined. The alumina carrier may be subjected to intermediate treatments during its preparation, including washing with water or a solution of ammonium hydroxide, for example, which treatments are well-known in the art.

The catalytic composite of our invention also contains a halogen component. The halogen component may be either fluorine, chlorine, bromine or iodine or mixtures thereof. Chlorine and bromine are the preferred halogen components. The halogen component is generally present, we believe, in a combined state with the porous carrier material. Preferably the halogen component is well dispersed throughout the catalytic composite. The halogen component will comprise from more than 0.2 weight % to about 15 weight %, calculated on an elemental basis, of the final catalytic composite. Preferably the catalyst comprises about 1 to 3 weight % chlorine.

The halogen component may be incorporated in the catalytic composite in any suitable manner, either during the preparation of the carrier material or before, while or after other catalytic components are incorporated. For example, the alumina sol utilized to form the preferred aluminum carrier material may contain halogen and thus contribute at least some portion of the halogen content in the final catalyst composite. Also, the halogen component or a portion thereof may be added to the catalyst composite during the incorporation of the carrier material with other catalyst components, for example, by using chloroplatinic acid to impregnate the platinum component. Also, the halogen component or a portion thereof may be added to the catalyst composite by contacting the catalyst with the halogen or a compound, solution, suspension or dispersion containing the halogen before or after other catalyst components are incorporated with the carrier material. Suitable compounds containing the halogen include acids containing the halogen, for example, hydrochloric acid. Or, the halogen component or a portion thereof may be incorporated by contacting the catalyst with a compound, solution, suspension or dispersion containing the halogen in a subsequent catalyst regeneration step. In the regeneration step carbon deposited on the catalyst as coke during use of the catalyst in a hydrocarbon conversion process is burned off the catalyst and the platinum group component on the catalyst is redistributed to provide a regenerated catalyst with performance characteristics much like the fresh catalyst. The halogen component may be added during the carbon burn step or during the platinum group component redistribution step, for example, by contacting the catalyst with a hydrogen chloride gas. Also, the halogen component may be added to the catalyst composite by adding the halogen or a compound, solution, suspension or dispersion containing the halogen, such as propylene dichloride, for example, to the hydrocarbon feed stream or to the recycle gas during operation of the hydrocarbon conversion process.

In contradistinction to the dehydrogenation catalysts of the prior art, the catalyst composite of our invention comprises more than 0.2 weight %, calculated on an elemental basis, of a halogen component. In the prior art dehydrogenation catalysts comprising a platinum group component and an alkali or alkaline earth component wherein the atomic ratio of the alkali or alkaline earth component to the platinum group component is more than 10, on the other hand, the halogen component was purposely eliminated entirely or otherwise maintained at the lowest possible level. This was accomplished generally by treating the catalyst with a stream of high temperature steam or a mixture of steam and a diluent such as air or hydrogen or nitrogen to remove the halogen component. In any event, the prior art dehydrogenation catalysts maintained the halogen component at less than 0.2 weight % of the catalyst composite, calculated on an elemental basis.

The halogen component in the catalyst of our invention is an active catalyst component. The active halogen component helps improve the activity of our catalyst for dehydrogenating hydrocarbons. Also, the active halogen component helps suppress carbon formation on our catalyst during its use in a dehydrogenation process. These advantages are obtained with our catalyst without increased undesirable isomerization or cracking side reactions taking place, that is, the selectivity of our catalyst is about the same as for prior art dehydrogenation catalysts.

Optionally the catalyst of our invention may also contain a sulfur component. Generally the sulfur component will comprise about 0.01 to 10 weight %, calculated on an elemental basis, of the final catalytic composite. The sulfur component may be incorporated into the catalytic composite in any suitable manner. Preferably sulfur or a compound containing sulfur such as hydrogen sulfide or a lower molecular weight mercaptan, for example, is contacted with the catalyst composite in the presence of hydrogen at a hydrogen to sulfur ratio of about 100 and a temperature of from about 10° to about 540° C., preferably under water-free conditions, to incorporate the sulfur component.

Optionally, the catalyst may also contain other, additional components or mixtures thereof which act alone or in concert as catalyst modifiers to improve catalyst activity, selectivity or stability. Some well-known catalyst modifiers include antimony, arsenic, beryllium, bismuth, cadmium, calcium, chromium, cobalt, copper, gallium, gold, indium, iron, lithium, manganese, molybdenum, nickel, rhenium, scandium, silver, tantalum, thallium, titanium, tungsten, uranium, zinc, and zirconium. These additional components may be added in any suitable manner to the carrier material during or after its preparation, or they may be added in any suitable manner to the catalytic composite either before, while or after other catalytic components are incorporated.

Preferably the catalyst of our invention is nonacidic. "Nonacidic" in this context means that the catalyst has very little skeletal isomerization activity, that is, the catalyst converts less than 10 mol % of butene-1 to isobutylene when tested at dehydrogenation conditions and, preferably, converts less than 1 mol %. The acidity of the catalyst can be decreased if necessary to make the catalyst nonacidic by increasing the amount of the alkali or alkaline earth component within our claimed range, or by treating the catalyst with steam to remove some of the halogen component within our claimed range.

After the catalyst components have been combined with the porous carrier material, the resulting catalyst composite will generally be dried at a temperature of from about 100° to about 320° C. for a period of typically about 1 to 24 hours or more and thereafter calcined at a temperature of about 320° to about 600° C. for a period of about 0.5 to about 10 or more hours. Finally the calcined catalyst composite is typically subjected to a reduction step before use in the hydrocarbon conversion process. This reduction step is effected at a temperature of about 230° to about 650° C. for a period of about 0.5 to about 10 or more hours in a reducing environment, preferably dry hydrogen, the temperature and time being selected to be long and hot enough to reduce substantially all of the platinum group component to the elemental metallic state.

According to one process dehydrogenatable hydrocarbons are contacted with the catalytic composite of our invention in a dehydrogenation zone maintained at dehydrogenation conditions. This contacting may be accomplished in a fixed catalyst bed system, a moving catalyst bed system, a fluidized bed system, etc., or in a batch-type operation. A fixed bed system is preferred. In this fixed bed system the hydrocarbon feed stream is preheated to the desired reaction temperature and then passed into the dehydrogenation zone containing a fixed bed of the catalyst. The dehydrogenation zone may itself comprise one or more separate reaction zones with heating means therebetween to ensure that the desired reaction temperature can be maintained at the entrance to each reaction zone. The hydrocarbon may be contacted with the catalyst bed in either upward, downward or radial flow fashion. Radial flow of the hydrocarbon through the catalyst bed is preferred for commercial scale reactors. The hydrocarbon may be in the liquid phase, a mixed vapor-liquid phase or the vapor phase when it contacts the catalyst. Preferably it is in the vapor phase.

Conditions in the dehydrogenation zone include a temperature of from about 400° to about 900° C., a pressure of from about 0.01 to 10 atmospheres and a liquid hourly space velocity (LHSV) of from about 0.1 to 100 hr.$^{-1}$. Generally for normal paraffins the lower the molecular weight the higher the temperature required for comparable conversion. The pressure in the dehydrogenation zone is maintained as low as practicable, consistent with equipment limitations, to maximize the chemical equilibrium advantages.

The effluent stream from the dehydrogenation zone generally will contain unconverted dehydrogenatable hydrocarbons, hydrogen and the products of dehydrogenation reactions. This effluent stream is typically cooled and passed to a hydrogen separation zone to separate a hydrogen-rich vapor phase from a hydrocarbon-rich liquid phase. Generally, the hydrocarbon-rich liquid phase is further separated by means of either a suitable selective adsorbent, a selective solvent, a selective reaction or reactions or by means of a suitable fractionation scheme. Unconverted dehydrogenation hydrocarbons are recovered and may be recycled to the dehydrogenation zone. Products of the dehydrogenation reactions are recovered as final products or as intermediate products in the preparation of other compounds.

The dehydrogenatable hydrocarbons may be admixed with a diluent material before, while or after being passed to the dehydrogenation zone. The diluent material may be hydrogen, steam, methane, ethane, carbon dioxide and the like. Hydrogen is the preferred diluent. Ordinarily, when hydrogen is utilized as the diluent it is utilized in amounts sufficient to ensure a hydrogen to hydrocarbon mol ratio of about 0.1:1 to about 40:1, with best results being obtained when the mol ratio range is about 1:1 to about 10:1. The diluent hydrogen stream passed to the dehydrogenation zone will typically be recycled hydrogen separated from the effluent from the dehydrogenation zone in the hydrogen separation zone.

Water or a material which decomposes at dehydrogenation conditions to form water such as an alcohol, aldehyde, ether or ketone, for example, may be added to the dehydrogenation zone, either continuously or intermittently, in an amount to provide, calculated on the basis of equivalent water, about 1 to about 20,000 weight ppm of the hydrocarbon feed stream. About 1 to about 10,000 weight ppm of water addition gives best results when dehydrogenating paraffins having from 6 to 30 more carbon atoms.

The following worked Examples are introduced to describe further the catalyst of our invention and to teach one skilled in the art how to make it and how to use it in the hydrocarbon conversion process of our invention. These Examples represent several specific embodiments of our invention and are intended to be illustrative only and not restrictive.

EXAMPLE I

A catalyst composite, hereinafter catalyst "A", was prepared to represent a catalyst according to our invention. It comprised about 0.8 weight % platinum, about 0.5 weight % tin, about 2.7 weight % potassium and about 1.3 weight % chlorine on a carrier of gamma-alumina. The atomic ratio of potassium to platinum for this catalyst was about 16.8. The catalyst was prepared by dissolving substantially pure aluminum pellets in a hydrochloric acid solution, thereafter dissolving in this sol an amount of stannic chloride calculated to provide a final composite containing about 0.5 weight % tin, and then stirring the sol vigorously to distribute the tin component evenly throughout it. Hexamethylenetetramine was then added to the sol and the resulting mixture was dropped into an oil bath in a manner to form spherical particles having an average particle diameter of about 1/16 inch. Thereafter the spheres were aged and washed with an ammoniacal solution, then dried and calcined to form a spherical gamma-alumina carrier material containing about 0.5 weight % tin in the form of tin oxide. More details about this method of preparing the preferred alumina carrier material are disclosed in U.S. Pat. No. 2,620,314.

Then, 333 g (600 cc) of the tin-containing alumina carrier was contacted with 600 cc of a deionized water solution containing chloroplatinic acid equivalent to the specified weight % of platinum and hydrochloric acid equivalent to 2 weight % of the alumina in a rotary drier for 15 minutes at room temperature. Then steam was passed to the jacket of the drier and the water was driven off under a nitrogen purge for 2–3 hours, leaving the platinum component and some chlorine component incorporated with the tin-containing alumina carrier. The chlorine component present was then removed by treating the platinum, tin and halogen-containing composite at 550° C. with 300 hr.$^{-1}$ gas hourly space velocity (GHSV) of a 50/50 air 80° C. steam mixture for 6 hours. After this treatment with steam the composite contained less than 0.1 weight % chlorine. Then, the platinum and tin-containing composite was contacted with a deionized water solution containing potassium nitrate equivalent to the specified weight % of potassium and dried to incorporate the potassium component. Then, 220 cc of the platinum, tin and potassium-containing composite was heated to 110° C. in 1000 hr.$^{-1}$ GHSV of dry air for ½ hour, the temperature was raised to 525° C. and 12 cc per hour of 0.9 M hydrochloric acid was added with 300 hr.$^{-1}$ GHSV of a 50/50 air/80° C. steam mixture for 3 hours to incorporate the halogen component. Finally, the platinum, tin, potassium and chlorine-containing composite was dried at 525° C. and 1000 hr.$^{-1}$ GHSV of dry air for ½ hour. This catalyst "A" represents one preferred embodiment of our catalyst composite.

A different catalyst, hereinafter catalyst "B" was prepared to represent the dehydrogenation catalysts of the prior art wherein the halogen content was maintained at less than 0.2 weight %. This catalyst comprised about 0.8 weight % platinum, about 0.5 weight % tin, about 2.7 weight % potassium and about 0.09 weight % chlorine on a carrier of gamma alumina. Catalyst "B" was prepared in the same manner as catalyst "A" above, except the chlorine component from the hydrochloric acid, required at more than 0.2 weight % for the catalyst "A" of our invention was not added to catalyst "B".

Catalysts "A" and "B" both contained a small amount of sulfur component which was incorporated in a sulfiding step at 625° C. and 1 atmosphere pressure from a 1% mixture of hydrogen sulfide in hydrogen gas at 850 hr.$^{-1}$ gas hourly space velocity (GHSV) for 7 hours. After the sulfiding step these catalysts contained approximately 1 weight % sulfur, calculated on an elemental basis.

These catalysts were also reduced in a reduction step prior to being tested. Reduction conditions were; 625° C. and 1 atmosphere pressure in hydrogen gas at 700 hr.$^{-1}$ GHSV for 1 hour.

These catalysts were then tested for dehydrogenation activity, selectivity and stability in a laboratory scale dehydrogenation plant comprising a reactor, a hydrogen separation zone, and heaters, coolers, pumps, compressors, and the like conventional equipment for handling hydrocarbons. In this plant, the feed stream containing the dehydrogenatable hydrocarbon is combined with a hydrogen gas stream and the resulting mixture is heated to the desired conversion temperature which is measured at the inlet to the dehydrogenation reactor. The heated mixture then contacts the fixed bed of catalyst in down flow fashion. The pressures reported herein are measured at the outlet from the reactor. An effluent stream is withdrawn from the reactor and cooled. A portion of the effluent stream is collected and analyzed to measure the amount of conversion, or activity, and the relative amount of desired dehydrogenated hydrocarbons, or selectivity, for the catalyst composite being tested. Conversion numbers reported herein are calculated on the basis of disappearance of isobutane, expressed in weight %, of the feed stream. Similarly, selectivity numbers reported are calculated on the basis of desired isobutylene produced, expressed in mol %, of the isobutane converted.

The same isobutane feed stream was used in both tests. It comprised in weight %;

isobutane: 99.85 normal butane: 0.10 propane: 0.05

Reaction conditions were the same for both tests. They were; 625° C., 2 atmospheres, 2 hydrogen to hydrocarbon mol ratio and 11.2 hr.$^{-1}$ LHSV. Results from the tests are presented in FIGS. 1 and 2.

Figure 2:
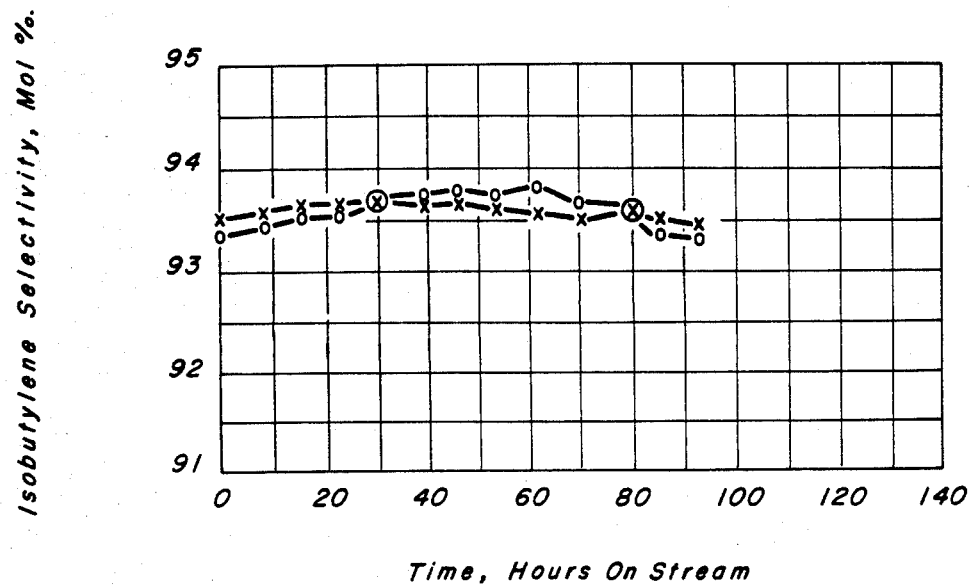

FIG. 1 clearly shows that the catalyst of our invention, catalyst "A" comprising a platinum group component, an alkali or alkaline earth component, more than 0.2 weight %, calculated on an elemental basis, of a halogen component and a porous carrier material, has more activity, represented by the higher weight % isobutane conversion, than the catalyst of the prior art, catalyst "B" comprising the same components except less than 0.2 weight % of the halogen component. FIG. 2 shows that the selectivity of our catalyst "A" is comparable to that of prior art catalyst "B".

Also, after 97 hours on stream the catalysts in this Example were removed from the reactor and analyzed for carbon to measure the amount of coke which had been deposited on catalyst during the test. Catalyst "A" of our invention contained 0.11 weight % carbon, calculated on an elemental basis. Catalyst "B" of the prior art, on the other hand, contained 0.39 weight % carbon, more than 3 times as much carbon as catalyst "A". So, the catalyst of our invention also helps to suppress coke deposition, which is one of the major causes of dehydrogenation catalyst deactivation, and longer catalyst life and less regeneration time are expected for our catalyst compared to the prior art catalysts.

EXAMPLE II

A catalyst composite, hereinafter catalyst "C", was prepared to represent also one catalyst of our invention. It comprised about 0.7 weight % platinum, about 0.5 weight % tin, about 2.8 weight % potassium and about 2.5 weight % chlorine on a carrier of gamma-alumina. The atomic ratio of potassium to platinum for this catalyst was about 20.0. The catalyst was prepared in substantially the same manner as catalyst "A" in Example I above. This catalyst "C" represents another preferred embodiment of our catalyst composite.

Another different catalyst, hereinafter catalyst "D" was prepared also to represent the dehydrogenation catalysts of the prior art wherein the halogen content was maintained at less than 0.2 weight %. This catalyst comprised about 0.7 weight % platinum, about 0.5 weight % tin, about 2.9 weight % potassium and about 0.1 weight % chlorine on a carrier of gamma-alumina. Catalyst "D" was prepared in substantially the same manner as catalyst "B" in Example I above, and the amount of the chlorine component, required at more than 0.2 weight % for the catalyst "C" of our invention, was maintained at about 0.1 weight %.

Catalysts "C" and "D" were both tested for dehydrogenation of ethane to ethylene in a laboratory plant like the plant in Example I. Reaction conditions for both tests were about from 680° to 720° C., 1.3 atmospheres, 1 hydrogen to hydrocarbon mol ratio and 5.0 hr.$^{-1}$ LHSV.

Figure 3:
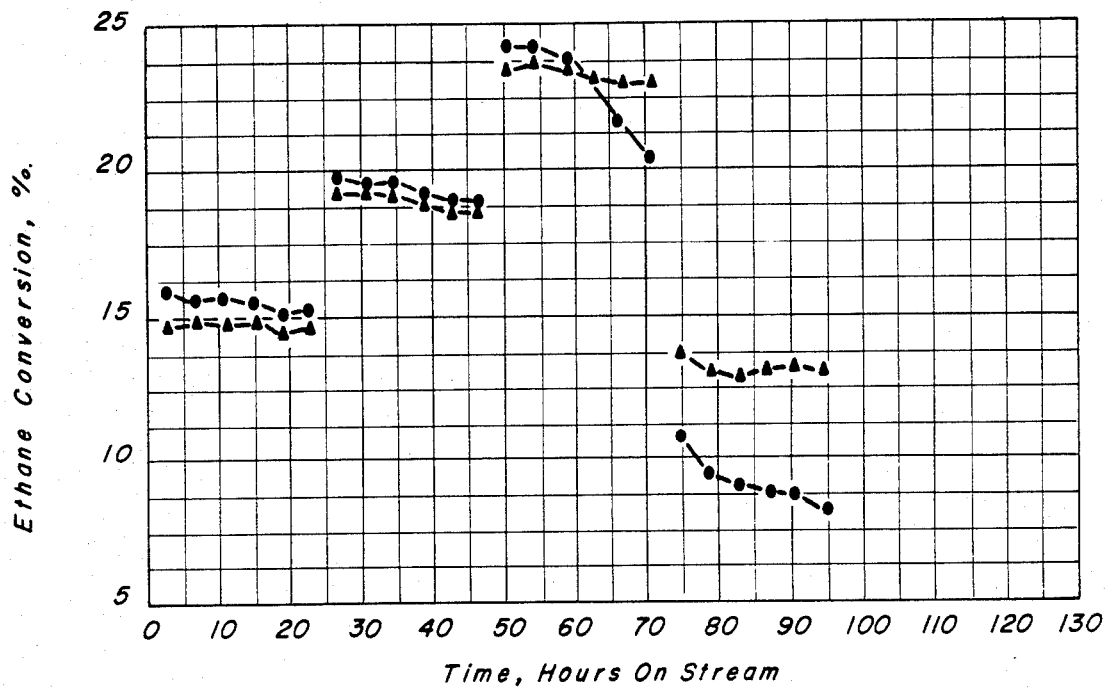
Figure 4:
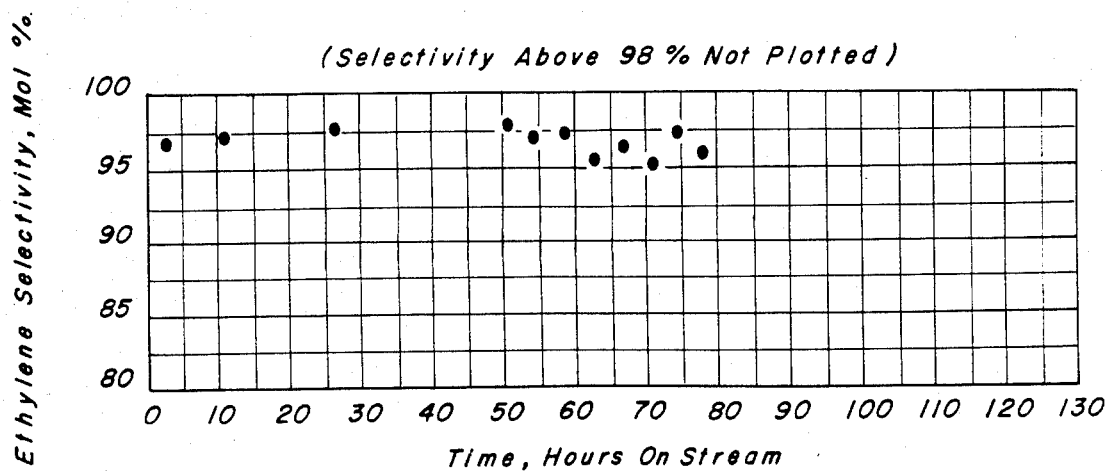

The tests consisted of 4 consecutive 25 hour periods; perios 1.) at 680° C., period 2.) at 700° C., period 3.) at 720° C. and period 4.) at 680° C. again. From FIG. 4 it can be seen that in all periods of the tests selectivity for both catalysts was more than 95 mol %. Generally, however, selectivity for our catalyst "C", at more than 98% for all the periods, was slightly higher than for prior art catalyst "D". From FIG. 3 it can be seen that in periods 1 and 2 these catalysts exhibited similar activity at about 15 and 19 average mol % conversion, respectively, and they exhibited similar activity stability throughout these periods. In period 3, however, at about 24 mol % conversion, activity stability for prior art catalyst "D" became notably worse than for our catalyst "C", and by the end of the period activity for catalyst "D", at about 20 mol % conversion, was notably worse also. Activity for catalyst "C" on the other hand, was stable at about 23 mol % conversion throughout the period. These trends continued in period 4 where activity for our catalyst "C" was stable at about 13 mol % conversion, and activity for prior art catalyst "D" fell from about 11 to about 8 mol % conversion. These tests suggest that in a commercial dehydrogenation process catalyst "C" of our invention will be more stable than catalyst "D" of the prior art.

Also, after 97 hours on stream the catalysts in this Example were removed from the reactor and analyzed for carbon. Catalyst "C" of our invention contained 8.7 weight % carbon, calculated on an elemental basis. Catalyst "D" of the prior art, on the other hand, contained 25.6 weight % carbon, nearly three times as much carbon as catalyst "C". This data suggests that in a commercial dehydrogenation process catalyst "C" of our invention will be more quickly and easily regenerated than catalyst "D" of the prior art.

EXAMPLE III

A catalyst composite, hereinafter catalyst "E", was prepared to represent also one catalyst of our invention. It comprised about 0.75 weight % platinum, about 0.5 weight % tin, about 2.8 weight % potassium and about 3.2 weight % chlorine on a carrier of gamma-alumina. The atomic ratio of potassium to platinum for this catalyst was about 18.6. The catalyst was prepared in substantially the same manner as catalyst "A" in Example I above. This catalyst "E" represents another preferred embodiment of our catalyst composite.

Another different catalyst, hereinafter catalyst "F" was prepared to represent the catalysts of the prior art wherein the atomic ratio of the alkali or alkaline earth component was maintained at less than or equal to 10. This catalyst comprised about 0.75 weight % platinum, about 0.5 weight % tin, about 1.4 weight % potassium and about 2.0 weight % chlorine on a carrier of gamma-alumina. The atomic ratio of potassium to platinum for this catalyst was about 9.3. Catalyst "F" was prepared in substantially the same manner as catalyst "E" except the amount of potassium added to catalyst "F" was maintained at the lower level to ensure an atomic ratio of potassium to platinum for this catalyst of less than or equal to 10.

Catalysts "E" and "F" were tested for dehydrogenation of isobutane to isobutylene in a laboratory plant like the plant in Example I. Reaction conditions were about 645° C., 2.0 atmospheres, 1.5 hydrogen to hydrocarbon mol ratio and 5.0 hr.$^{-1}$ LHSV. Results from the tests are presented in FIGS. 5 and 6.

Figure 5:
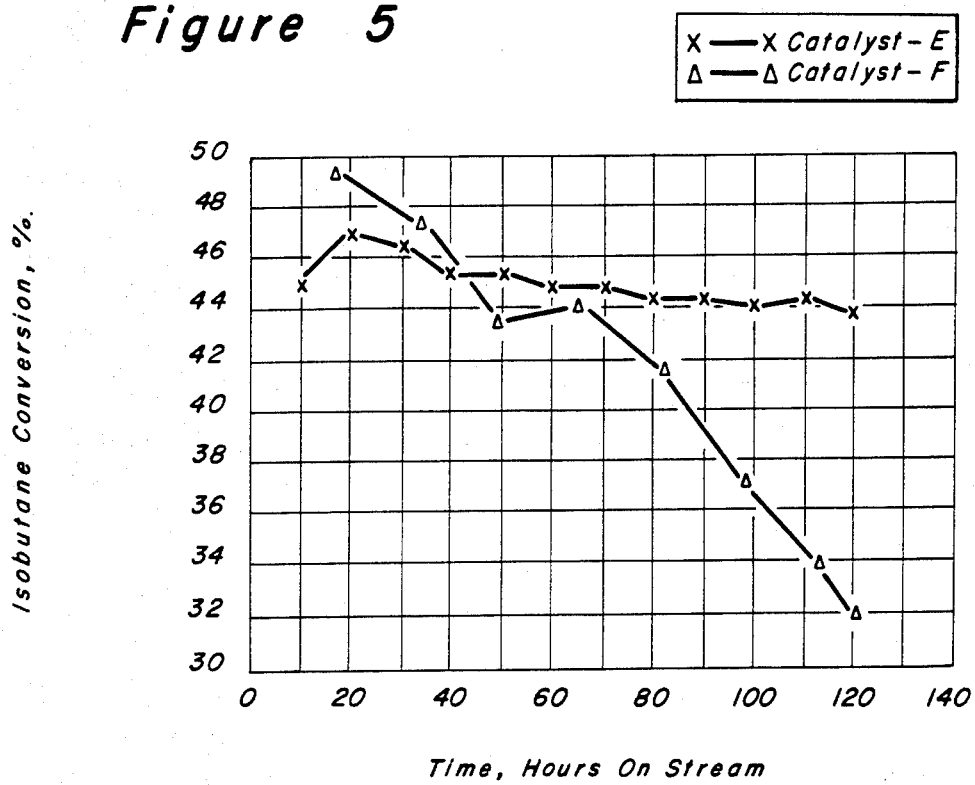
Figure 6:
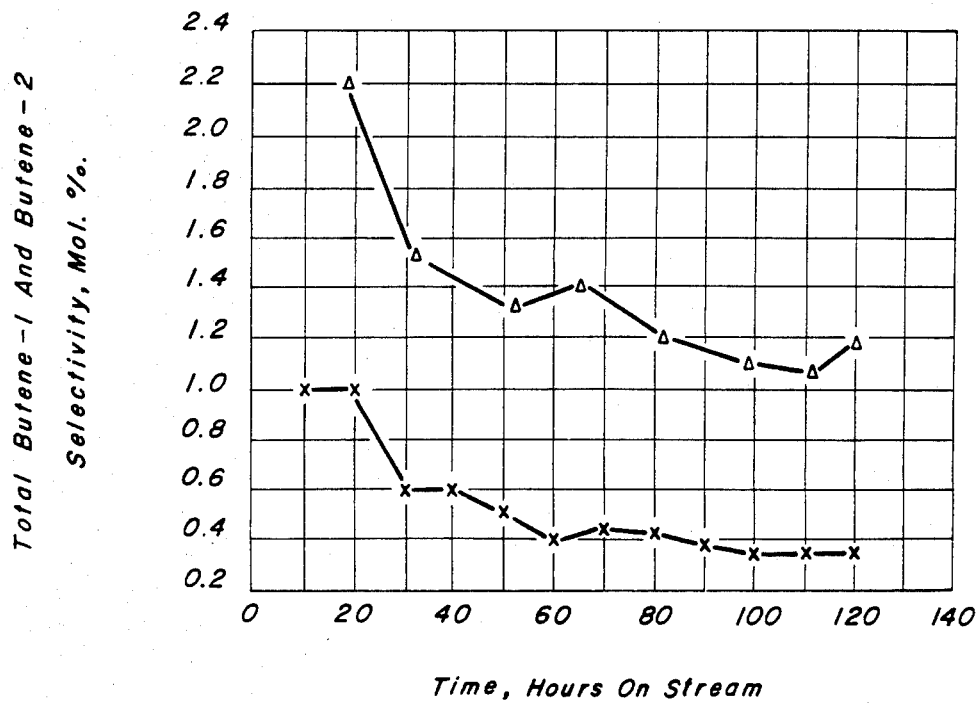

In FIG. 5 it can be seen that the dehydrogenation activity stability for our catalyst "E" is much greater than for prior art catalyst "F", represented by the much smaller change with time of the % isobutane conversion throughout the test for our catalyst "E". Also, in FIG. 6 it can be seen that the undesirable isomerization activity for our catalyst "E" is much less than for prior art catalyst "F", represented by the lower total butene-1 and butene-2 selectivity throughout the test for our catalyst "E". These tests suggest that in a commercial dehydrogenation process our catalyst "E" will be more stable and more selective than prior art catalyst "F".

What we claim is:

1. A catalyst composition comprising a platinum group component, a Group IVA component, an alkali or alkaline earth component, more than 0.2 weight %, calculated on an elemental basis, of a halogen component and a porous carrier material, wherein the atomic ratio of the alkali or alkaline earth component to the platinum group component is more than 10.

2. The composition of claim 1 wherein said platinum group component comprises platinum.

3. The composition of claim 1 wherein said Group IVA component comprises tin.

4. The composition of claim 1 wherein said alkali or alkaline earth component comprises potassium.

5. The composition of claim 1 wherein said halogen component comprises chlorine.

6. The composition of claim 1 wherein said porous carrier material comprises alumina.

7. The composition of claim 1 wherein the atomic ratio of the alkali or alkaline earth component to the platinum group component is from about 15 to about 25.

8. The composition of claim 1 which comprises a platinum component, a tin component, a potassium component and a chlorine component with alumina.

9. The composition of claim 1 which comprises a platinum component, a tin component, a lithium component and a chlorine component with alumina.

10. The composition of claim 1 which comprises a platinum component, a lithium component, a cesium component and a chlorine component with alumina.

11. The composition of claim 1 which comprises a platinum component, a tin component, an indium component, a lithium component and a chlorine component with alumina.

12. The composition of claim 1 which also comprises a sulfur component.

13. A method for making a catalyst which comprises incorporating a platinum group component, a Group IVA component, an alkali or alkaline earth component and more than 0.2 weight %, calculated on an elemental basis, of a halogen component with a porous carrier material so that the atomic ratio of the alkali or alkaline earth component to the platinum group component is more than 10.

14. The method of claim 13 wherein the Group IVA component is tin which is cogelled with the porous carrier material.

* * * * *